United States Patent [19]

Melera et al.

[11] 4,403,147
[45] Sep. 6, 1983

[54] APPARATUS FOR ANALYZING LIQUID SAMPLES WITH A MASS SPECTROMETER

[75] Inventors: Attilio Melera, Los Altos; Armand Neukermans, Palo Alto, both of Calif.

[73] Assignee: Hewlett-Packard Company, Palo Alto, Calif.

[21] Appl. No.: 348,129

[22] Filed: Feb. 12, 1982

Related U.S. Application Data

[60] Division of Ser. No. 215,787, Dec. 12, 1980, abandoned, which is a continuation of Ser. No. 42,477, May 25, 1979, abandoned.

[51] Int. Cl.³ .......................................... H01J 49/30
[52] U.S. Cl. ................................... 250/288; 250/281; 73/61.1 C
[58] Field of Search ............................. 250/288, 281; 73/61.1 C; 210/198.2

[56] References Cited

U.S. PATENT DOCUMENTS

| 3,944,826 | 3/1976 | Gray | 250/288 |
| 3,997,298 | 12/1976 | McLafferty et al. | 73/61.1 C |
| 4,160,161 | 7/1979 | Horton | 250/281 |
| 4,209,696 | 6/1980 | Fite | 250/281 |
| 4,300,044 | 11/1981 | Iribarne et al. | 250/288 |

FOREIGN PATENT DOCUMENTS 1339448 12/1973 United Kingdom.

OTHER PUBLICATIONS

Walisch et al., "Rapid, Continuous Transfer of Liquid Into a Mass Spectrometer", Talanta, 22, pp. 517–521, Pergamon Press, Great Britain, 1975.
Sawdo et al., "Refrigerated Direct Insertion Probe for Mass Spectrometry", Anal. Chem., 48 (4), Apr. 1976, pp. 790–791.

Primary Examiner—Alfred E. Smith
Assistant Examiner—Carolyn E. Fields
Attorney, Agent, or Firm—Jeffery B. Fromm; Ronald E. Grubman

[57] ABSTRACT

Apparatus is provided for analyzing liquid samples by a mass spectrometer. A stream of liquid droplets of the sample is formed by a probe which expels the droplets into a desolvation chamber. The droplets are evaporated in the desolvation chamber and the evaporated materials injected into the source region of the mass spectrometer. In some preferred embodiments, the system is configured so that no solvent or solute is pumped out of the desolvation chamber during transit; discrimination against highly volatile materials is thereby prevented. The apparatus may be used as an interface between a liquid chromatograph and the mass spectrometer.

14 Claims, 2 Drawing Figures

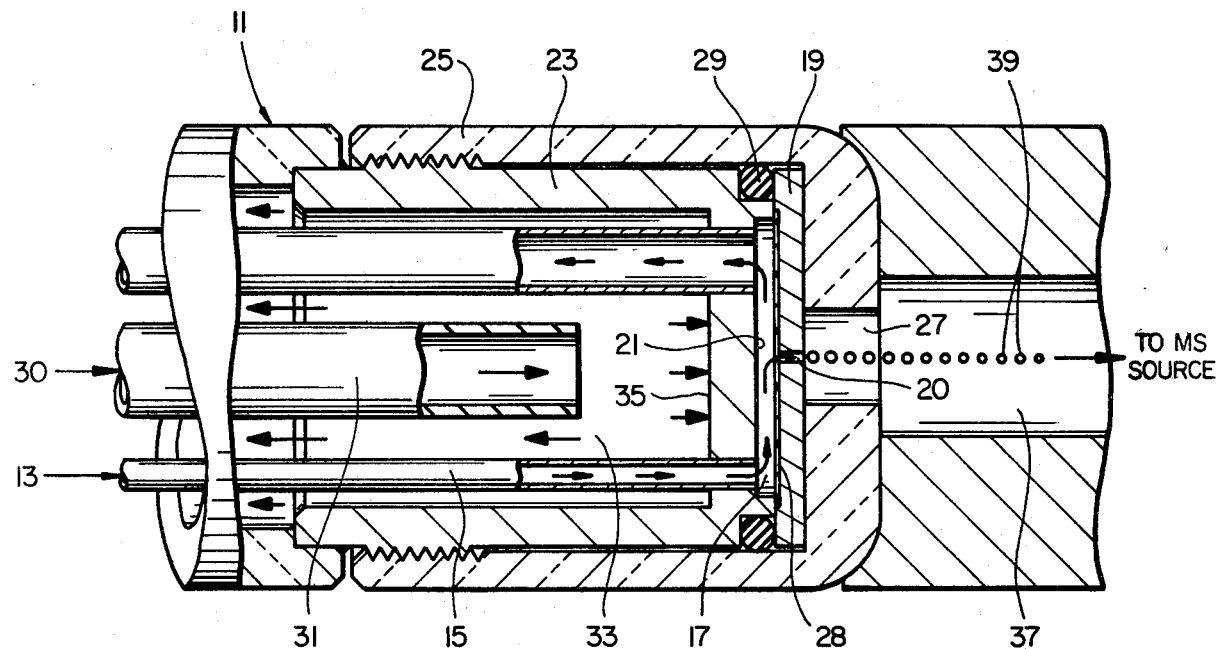
FIG_1
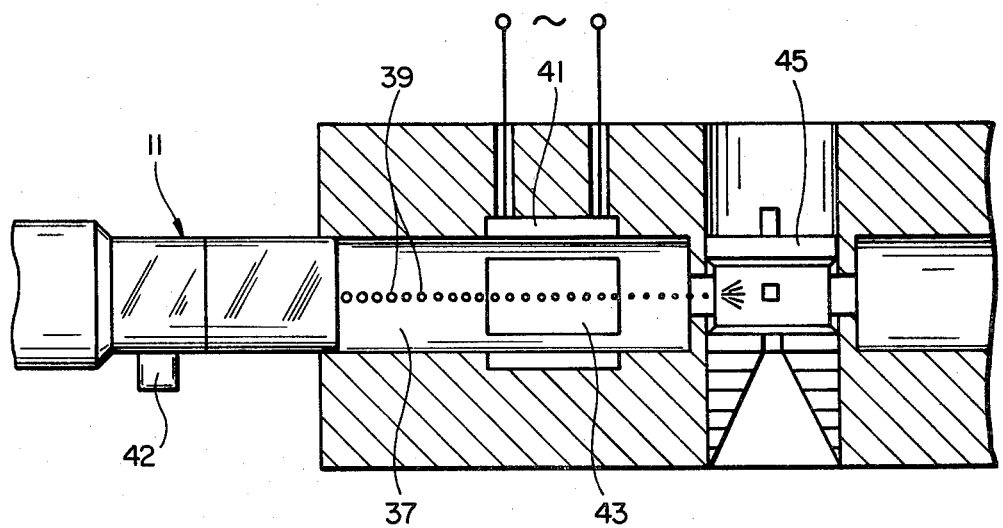
FIG_2

APPARATUS FOR ANALYZING LIQUID SAMPLES WITH A MASS SPECTROMETER

CROSS REFERENCE TO RELATED APPLICATION

This is a division of application Ser. No. 215,787, filed Dec. 12, 1980, now abandoned, which was a continuation of Ser. No. 042,477, filed May 25, 1979, also now abandoned.

BACKGROUND OF THE INVENTION

This invention is concerned with the introduction of liquid samples into the source region of a mass spectrometer. The invention has particular applicability as an interface between the output of a liquid chromatograph (LC) and a mass spectrometer, enabling the use of the mass spectrometer as an analyzer for the LC. There has recently been much effort devoted to this problem, a summary of which is provided in the paper entitled, "On-Line Liquid Chromtography Mass Spectrometry: The Monitoring of HPLC Effluents by a Quadrapole Mass Spectrometer and a Direct Liquid Inlet Interface (DLI)", published by Patrick J. Arpino, in the Instrumental Applications in Forensic Drug Chemistry Proc. Int. Symp., May 29-30, 1978, edited by Klein, Kruegel, and Sobol.

Among the methods mentioned in that article for introducing the LC effluent into the mass spectrometer are several in which the liquid leaving the LC is instantly vaporized at or near the tip of a capillary tube; the same is thereby introduced into the mass spectrometer source in gaseous form. Such a system is also described in U.S. Pat. No. 3,997,298 entitled, "Liquid Chromatography—Mass Spectrometry System and Method", issued Dec. 14, 1976, to F. W. McLafferty, et al. It has been found to be a deficiency in such systems that the capillary frequently becomes plugged with residue of the sample and the solvent in which the sample is dissolved; this occurs apparently because of evaporation at the solvent-vapor interface within the capillary tip when the temperature rises above the solvent boiling point. Another prior art system in which the liquid is heated and vaporized is discussed by H. R. Udseth, R. G. Orth, and J. H. Futrell, in a paper entitled, "An LC-MS Interface" presented at the Annual Conference on Mass Spectrometry in St. Louis, Missouri, in June 1978.

A different system is discussed by Tsuge, Hirata, and Takeuchi in an article entitled, "Vacuum Nebulizing Interface for Direct Coupling of Micro-Liquid Chromatograph and Mass Spectrometer", published in *Analytical Chemistry*, Volume 51, No. 1, January 1979. In this system, a high velocity carrier gas streams by the liquid to form an aerosol, which is then sprayed into a pumping region, where the higher volatility solvent is pumped out. This system may prove to be disadvantageous in that it discriminates in favor of materials of low volatility, more highly volatile materials being preferentially pumped away together with the solvent.

SUMMARY OF THE INVENTION

In accordance with the illustrated preferred embodiments, the present invention provides an apparatus for analyzing liquid samples by a mass spectrometer. A highly directional jet of very fine liquid droplets containing the sample to be analyzed is first created. The liquid jet is evaporated prior to injection into the mass spectrometer, which, in preferred embodiments, is accomplished by spraying the jet into a desolvation chamber located upstream of the source region of the mass spectrometer. If the mass spectrometer is being utilized to analyze the effluent from a liquid chromatograph, the droplets will consist of the solute under analysis dissolved in the carrier solvent. The stream of liquid droplets evaporates as it passes through the desolvation chamber, so that a gaseous mixture of solvent and solute molecules enter the mass spectrometer source. The solvent may be selected so that the mass spectrometer will produce a chemical ionization (CI) spectrum characterstic of the solute to be analyzed. In accordance with the invention, evaporation of the liquid droplets takes place during transit through the desolvation chamber. When used in conjunction with an LC, the present invention solves the problem of "plugging up" encountered by prior art systems, since the liquid is not vaporized at or near the tip of the LC output.

In some preferred embodiments, the system is configured so that no solvent or solute is pumped out of the desolvation chamber during transit; discrimination against highly volatile materials is thereby prevented.

DESCRIPTION OF THE DRAWINGS

FIG. 1 shows a probe and desolvation chamber by means of which liquid samples can be analyzed with a mass spectrometer.

FIG. 2 illustrates an embodiment of the invention in which the length of the desolvation chamber may be varied.

DETAILED DESCRIPTION OF THE PREFERRED EMBODIMENT

In FIG. 1 there is shown an interface probe 11 of the general type which was disclosed by J. Serum and A. Melera in a paper entitled, "A New LC-MS System" presented at the ASNS Meeting on June 1, 1978. A liquid sample 13 is injected into probe 11; for example, the liquid may be the effluent output of a liquid chromatograph (LC) system. Sample 13 is transmitted through a column 15 into a chamber 17, which is essentially a volumetric region whose boundaries are defined by a metallic diaphragm 19 on one side and a surface 21 of a retaining element 23 on the other side. Diaphragm 19 includes a centrally positioned hole 20 therein with an inside diameter typically in the range of $5\mu$-$25\mu$. Diaphragm 19 is held in place by means of a cap 25 which is threaded onto retaining element 23. Cap 25 also includes a centrally positioned hole 27 of inside diameter about 0.005"-0.025". An O-ring 29 provides a vacuum seal. It is advantageous to include a filter to preclude clogging of orifice 20, e.g., a thin filter element 28, of porous Teflon may be positioned at the entrance to orifice 20 as shown.

The temperature in chamber 17 is controlled to keep the liquid solution in the chamber below its boiling point, in order that the solution will emerge in liquid droplet form rather than being evaporated into gaseous form. Temperature control may be accomplished by circulating a liquid 30 (for example, water) through a channel 31 into a region 33 in contact with chamber 17 through a wall 35 of retaining element 23. As indicated by the large arrows in FIG. 1, water circulates into the apparatus through channel 31 and back out through a larger channel, a portion of which is labeled 33.

The above-described probe 11 may be used as a component in the present invention by selecting the size of orifice 20 in diaphragm 19, the flow rate of sample 13, and the temperature of the coolant flowing in channel 31 so that a jet of very fine liquid droplets is continuously formed and sprayed out of probe 11 through opening 27. In a preferred embodiment, droplets of size in the range 10 $\mu$m–50 $\mu$m are produced using an orifice 20 of size in the range of 5 $\mu$m–20 $\mu$m, along with a sample flow rate in the range 15 $\mu$l/min–40 $\mu$l/min and a water temperature in the range 10° C.–40° C. Probe 11 is brought into contact with a desolvation chamber 37. By a desolvation chamber is meant a chamber in which the droplets evaporate under the influence of elevated temperature and low pressure as they traverse the chamber, forming a gaseous mixture of solvent and solute. Thus, a jet stream of liquid droplets 39 is emitted from probe 11 into chamber 37, which should have non-reactive walls, such as of gold. The temperature and pressure in chamber 37 are preferentially regulated so that the liquid droplets are not permitted to "freeze". In the embodiments illustrated in FIGS. 1 and 2, the pressure in chamber 37 is essentially determined by the rate of liquid flow into chamber 37 from probe 11 in conjunction with the rate of flow of gas out of chamber 37 into the MS source region (labeled 45 in FIG. 2). In an exemplary case of jet stream consisting of cortisol as a solute dissolved in a solvent of acetonitrile/water in a 1:1 ratio, temperatures in the range of 250° C.–350° C. combined with pressures in the range 10 Torr–50 Torr are appropriate. The length of chamber 37 is chosen to obtain an optimal desolvation pattern for droplets of different solute composition, size, or droplet frequency. For the solute and solvent described above, good results were obtained with a chamber of length about 2.0 cm.

FIG. 2 illustrates an embodiment in which the length of chamber 37 is variable by providing that probe 11 be inserted into chamber 37 up to a desired depth. For example, a mechanical connection such as a threaded connector between probe 11 and chamber 37 may be used which allows for adjustment of the insertion depth of probe 11 into desolvation chamber 37. Also shown in FIG. 2 is a heating element 41, e.g. an infrared heater which is used to control the temperature in the chamber. An accoustic transducer 42 (such as a piezoelectric transducer) may be used to stimulate probe 11 to break up the liquid stream into droplets of equal size. In this mode, the desolvation time for each droplet is the same as for all other droplets, so that no excess heating is required to evaporate large droplets.

It has been found, experimentally, that a tribo-electrical interaction between the liquid jet and the exit port from probe 11 can induce significant charging of the droplet stream. For example, a jet velocity of about 200 m/s produces a current of about 1 nanoamp at a liquid flow rate of 40 $\mu$l/min through orifice 20 of diameter 5 $\mu$m (for the exemplary solvent described above). This charging effect makes possible the inclusion of a set of electrostatic plates 43 to focus the particles into the mass spectrometer (MS) source 45. Another effect of the charging process is that the droplets tend to repel each other in flight, thereby minimizing particle coalescence. Moreover, as desolvation proceeds, the surface-charge density tends to increase and may exceed the surface tension area. At this point, the droplet explodes into smaller droplets, which process can be repeated again. The result is to speed up the evaporation process.

The preferred embodiments of FIGS. 1 and 2 illustrate another aspect of the invention; i.e., it is not required or necessary to "pump out" desolvation chamber 37 to produce evaporation. Thus, in these preferred embodiments, desolvation chamber 37 provides a closed region between probe 11 and MS source 45. Thus, all of the solute and solvent molecules in the jet stream may potentially be directed into MS source 45 after desolvation has occurred, with no discrimination against the more volatile components of the jet stream.

What is claimed is:

1. Apparatus for introducing a liquid solution of a solute dissolved in a solvent into the source region of a mass spectrometer, comprising:
   probe means for forming a stream of liquid droplets of said solution and expelling said stream from said probe means;
   vaporization means positioned between said probe means and the source region of said mass spectrometer for evaporating the solute and solvent in said droplets after said droplets have been expelled from said probe means, and directing at least some of the evaporated materials into said source region of the mass specctrometer; and
   temperature control means for maintaining the temperature in said probe means below the boiling point of said liquid solution in said probe means, to insure that said solution does not evaporate in or near said probe means and thereby plug said probe means.

2. Apparatus as in claim 1 wherein said temperature control means comprises a channel containing a cooling medium, said channel being in proximity to said probe means, to maintain the temperature in said probe means below the boiling point of said liquid solution in said probe means.

3. Apparatus as in claim 1 wherein:
   said vaporization means comprises a desolvation chamber adjacent said probe means, said stream of liquid droplets being expelled from said probe means into said desolvation chamber.

4. Apparatus as in claim 3 wherein:
   said desolvation chamber is configured to direct substantially all of said evaporated solute and solvent into said source region of the mass spectrometer.

5. Apparatus as in claim 4 wherein said probe means comprises:
   input means for accepting said liquid solution; and
   diaphragm means having an orifice therein in communication with said input means, said liquid solution being expelled from said orifice in the form of said stream of liquid droplets.

6. Apparatus as in claim 5 wherein said orifice has a diameter in the range 5 microns to 25 microns.

7. Apparatus as in claim 3 wherein said desolvation chamber is heated.

8. Apparatus as in claim 3 wherein said desolvation chamber can be varied in length.

9. Apparatus for introducing a liquid solution of a solute dissolved in a solvent into the source region of a mass spectrometer, comprising
   probe means for forming a stream of liquid droplets of said solution; and
   temperature control means for maintaining the temperature in said probe means below the boiling point of said solution in said probe means to insure that said solution does not evaporate in or near said probe means and thereby plug said probe means.

10. Apparatus as in claim 9 wherein said temperature control means comprises a channel containing a cooling medium, said channel being in proximity to said probe means to maintain the temperature in said probe means below the boiling point of said solution in said probe means.

11. Apparatus as in claim 9 wherein said probe means comprises:
input means for accepting said solution; and
diaphragm means having an orifice therein in communication with said input means, said solution being expelled from said orifice in the form of said stream of liquid droplets.

12. Apparatus as in claim 11 wherein said temperature control means comprises a channel containing a cooling medium, said channel being in proximity to said diaphragm means to maintain the temperature in the vicinity of said orifice below the boiling point of said solution in said probe means.

13. Apparatus as in claim 11 wherein said orifice has a diameter in the range 5 microns to 25 microns.

14. Apparatus as in claim 13 wherein said temperature control means comprises a channel containing a cooling medium, said channel being in proximity to said diaphragm means to maintain the temperature in the vicinity of said orifice below the boiling point of said solution in said probe means.

* * * * *